United States Patent
Swanson et al.

(10) Patent No.: US 6,879,857 B2
(45) Date of Patent: Apr. 12, 2005

(54) METHOD OF MANUFACTURING IMPLANTABLE TISSUE STIMULATING DEVICES

(75) Inventors: Lawrence Swanson, Lino Lakes, MN (US); Nick Youker, River Falls, WI (US); Stephen VanDerlick, Andover, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 412 days.

(21) Appl. No.: 10/236,628

(22) Filed: Sep. 6, 2002

(65) Prior Publication Data

US 2004/0049239 A1 Mar. 11, 2004

(51) Int. Cl.⁷ .............................................. A61N 1/375
(52) U.S. Cl. .......................................... 607/36; 607/37
(58) Field of Search .................................. 607/5, 36, 37

(56) References Cited

U.S. PATENT DOCUMENTS 6,493,212 B1 * 12/2002 Clarke et al. ................ 361/521
6,610,443 B2 * 8/2003 Paulot et al. ................ 429/181

FOREIGN PATENT DOCUMENTS

EP           1 148 562 A1 * 10/2001     ............ H01M/2/04

* cited by examiner

*Primary Examiner*—Carl Layno
(74) *Attorney, Agent, or Firm*—Thomas J. Nikolai; Nikolai & Mersereau, P.A.

(57) ABSTRACT

A method of fabricating implantable electronic medical devices eliminates the use of a backfill tube on the header or feed-through by reconfiguring the device's lead connector block anchor so as to provide it with a plug that can be used to seal an aperture in the device's header following removal of undesirable welding gases and replacement with an inert gas with a high breakdown resistance.

7 Claims, 4 Drawing Sheets

METHOD OF MANUFACTURING IMPLANTABLE TISSUE STIMULATING DEVICES

BACKGROUND OF THE INVENTION

I. Field of the Invention

This invention relates generally to the manufacture of implantable medical devices, such as cardiac rhythm management devices and neural stimulators, and more particularly to a method and apparatus for hermetically sealing electrical circuitry within a metal housing.

II. Discussion of the Prior Art

The typical implantable medical tissue stimulating device comprises a battery-powered pulse generator and a microprocessor-based controller within a hermetically sealed metal housing commonly referred to as the "can". The can generally comprises first and second halves that are joined together in a laser-welding operation about their perimeters after the battery power supply and electronic circuitry are inserted in the space defined by the two halves of the can. During the welding operation, a feed-through assembly is also welded in place on the can's header. The feed-through assembly includes a plurality of conductive wires extending through glass-to-metal seals so that electrical signals and stimulating pulses may be applied to and conveyed from the encased circuitry to terminal contacts within a lead connector block affixed to the outer surface of the header.

During the laser welding of the can, gases, notably argon and helium, are utilized. This gaseous atmosphere is subject to high voltage breakdown which can be detrimental to proper operation of the medical device. Thus, it is necessary to exhaust these gases from the can and replace them with a more inert gas exhibiting a significantly higher electrical breakdown resistance.

In accordance with prior art approaches, device backfilling with the inert gas has been done using tube stems that are located either on the feed-through assembly or on the case halves. The undesirable argon and helium are then exhausted through this tube and once exhausted, the interior of the can is backfilled with the inert gas, such as nitrogen. A small ball is then dropped into the tube to create a temporary seal, with the ball ultimately being welded in place. The tube stem utilized is relatively tall and thus necessarily increases the size and cost of the feed-through and the resulting implantable device. The size of the stem also may effect the available location of the feed-through in the device as well as the location of components that must be placed proximate the feed-through area due to arcing concerns. Furthermore, the routing of the feed-through wires is further complicated by the location of the tubular backfill stem in that the wires must be routed a safe distance away from the tube in order to prevent arcing. It is, therefore, desirable to provide a backfill approach allowing placement in an area of the header such that it does not interfere with other components or wire routing and which eliminates any arcing concerns.

As the complexity of implantable medical devices increases, there is an attendant increase in the number of feed-through wires required and thus, space on the feed-through is at a premium. It is therefore advantageous if the backfill tube can be eliminated from the feed-through assembly and the header.

It has also been a practice in the past to mechanically affix the lead connector block to the can's header using a suitable bonding agent. To hold the lead connector in place while the bonding agent cures, it has also been the practice to provide one or more anchors on the can's header which fit into preformed sockets in the base of the lead connector block. In order to accurately place the lead connector block anchors, it has been necessary to employ fixturing to accurately locate the anchor on the header prior to its being welded to the header. This fixturing necessarily increases the manufacturing costs.

The present invention provides a manufacturing method which dispenses with the need for a backfill tube on the header of the device housing by redesigning the anchor used in securing a lead connector block to the device's header. The anchor employed does not require the use of fixturing to properly position it on the device header prior to its being welded in place.

SUMMARY OF THE INVENTION

The method of manufacturing an implantable medical device in accordance with the present invention comprises welding first and second housing halves together about their perimeter with the device's electronic circuit and battery power supply disposed within the interior of the housing and welding the feed-through assembly to the housing header leaving an opening in the header that leads to the interior of the housing. The interior of the housing is then aspirated to exhaust those gases arising from the welding steps out through the opening. Next, an inert, relatively non-conductive gas is injected into the interior of the housing through the same opening. Following that, the opening is plugged with a modified anchor post that is then also used to anchor the lead connector block to the header.

The specially designed anchor post has a cylindrical midsection, an enlarged, frusto-conical head portion, a foot portion that is of a diameter that is a predetermined size greater than the size of the exhaust/refill opening and a plug portion that projects from the foot portion. The plug portion is of a size creating a friction fit when inserted into the opening. Because the foot portion of the anchor post is sized to be somewhat greater than the size of the opening in which the plug portion fits, the anchor post can be welded to the can's header without introducing unwanted gases, e.g., helium and argon, back into the interior of the can.

There are, of course, additional features of the invention that will be described hereinafter which will form the subject matter of the appended claims. Those skilled in the art will appreciate that the preferred embodiments may readily be used as a basis for designing other structures, methods and systems for carrying out the several purposes of the present invention. It is important, therefore, that the claims be regarded as including such equivalent constructions since they do not depart from the spirit and scope of the present invention. The foregoing and other features and other advantages of the invention will be apparent from the following more particular description of preferred embodiments of the invention, as illustrated in the accompanying drawings.

DESCRIPTION OF THE PREFERRED EMBODIMENT

Figure 1:
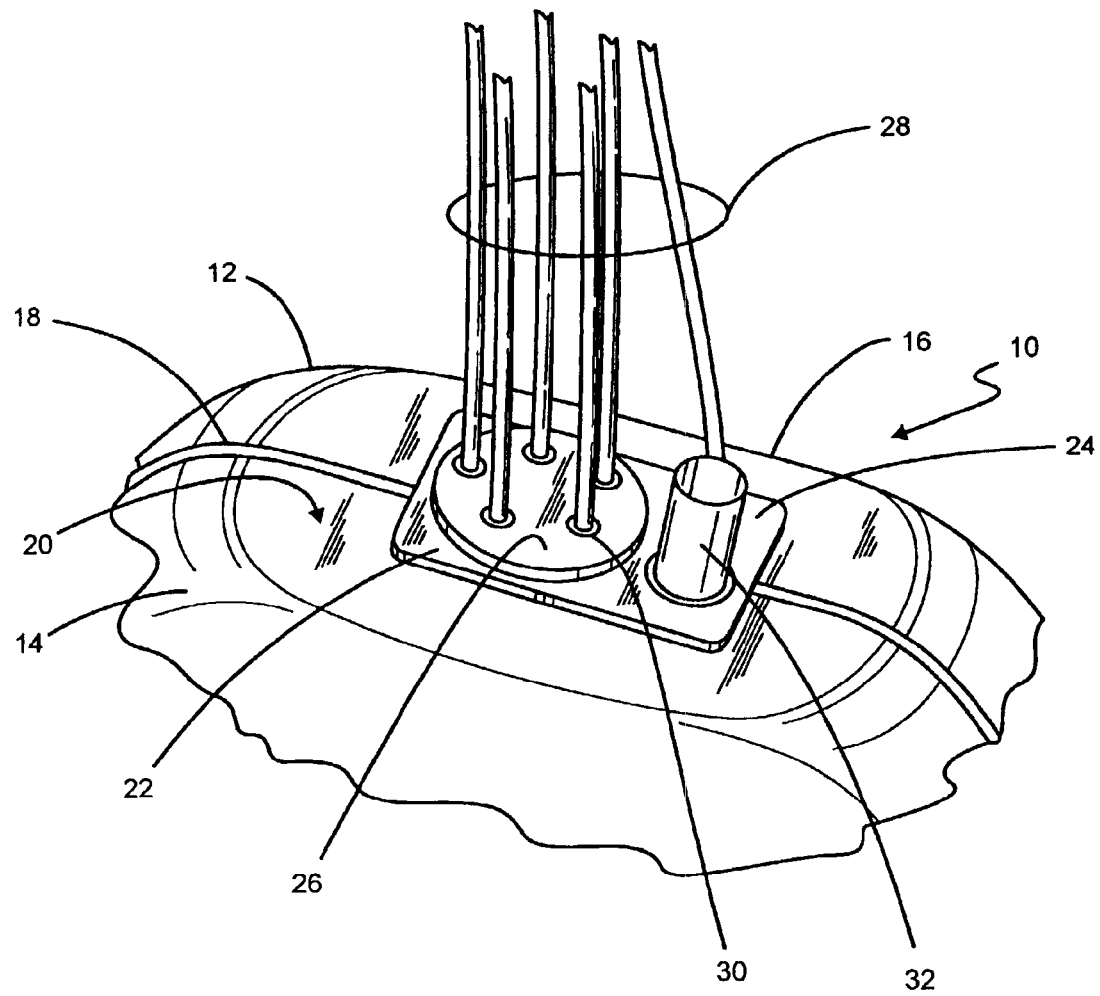
FIG. 1 shows a prior art feed-through and backfill tube assembly affixed to the header of an implantable electronic medical device.

Certain terminology will be used in the following description for convenience in reference only and will not be limiting. The words "upwardly", "downwardly", "rightwardly" and "leftwardly" will refer to directions in the drawings to which reference is made. The words "inwardly" and "outwardly" will refer to directions toward and away from, respectively, the geometric center of the device and associated parts thereof. Said terminology will include the words above specifically mentioned, derivatives thereof and words of similar import.

Referring first to FIG. 1, there is shown a prior art implantable medical device, such as a pacemaker/cardiac defibrillator, that is indicated generally by numeral 10. It includes a housing or can 12 that comprises a first half 14 and a second half 16, the halves being joined together in a laser welding operation along a seam line 18. The flat upper portion of the can 12 is referred to as the device's "header" and is identified generally by numeral 20. Welded to the header is a feed-through assembly 22 including a metal plate 24 on which is supported a ceramic disk 26 having a plurality of conductors 28 passing through glass-to-metal seals 30 into the interior of the housing or can 12. Also mounted on the feed-through assembly is a backfill tube 32 that is integral to the feed-through and through which unwanted gases resulting from the welding of the seam 18 is first exhausted. Once the unwanted gases have been eliminated, the interior of the can 12 is backfilled with a suitable gas, such as nitrogen. The nitrogen is also introduced through the backfill tube 32. To seal the backfill tube and prevent escape of the nitrogen, a small metal sphere is dropped into the interior of the tube 32. The interior walls of the tube 32 are tapered and the sphere seats therein so as to block the opening. Subsequently, the sphere is laser-welded within the tube 32 creating a permanent hermetic seal.

Figure 2:
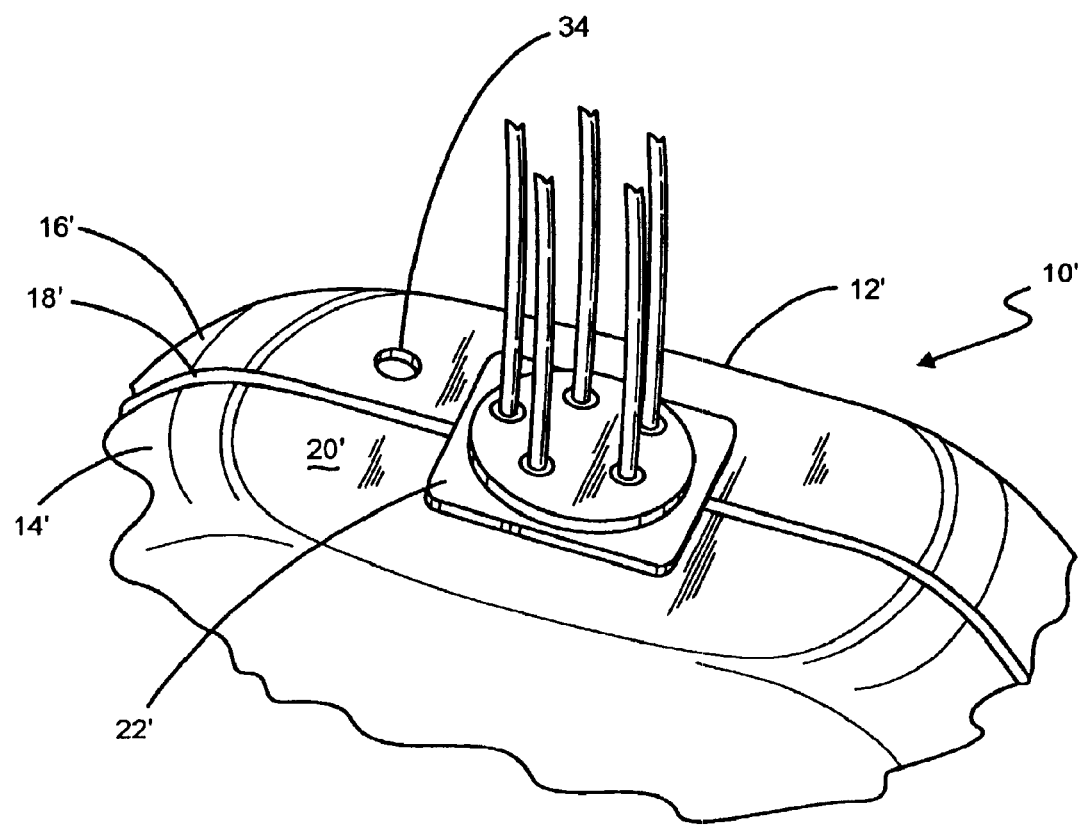
FIG. 2 is a top view of the header of an implantable medical device constructed in accordance with the method of the present invention.

Referring now to FIG. 2, the implantable medical device made in accordance with the method of the present invention is indicated generally by numeral 10' and it again comprises first and second housing halves 14' and 16' that are welded together about their mating perimeters along a seam line 18'. In the embodiment of FIG. 2, the feed-through assembly 22' does not require a backfill tube, such as tube 32 in the prior art drawing of FIG. 1. Instead, a small port or aperture 34 is provided through the header 20' leading to the interior of the can or housing 12'. After the seam 18' is formed and the feed-through assembly 22' is welded in place on the device's header, the interior of the housing is aspirated through the aperture 34 to exhaust unwanted gases resulting from the welding operation and following that, an inert, high breakdown resistant gas, such as nitrogen, is injected into the interior of the housing, via the port or aperture 34. The aperture 34 is then sealed.

In accordance with the present invention, the device used to seal the aperture 34 serves a dual purpose in that it also functions as the device's anchor for the lead connector block that is later bonded to the header 20'.

Figure 3:
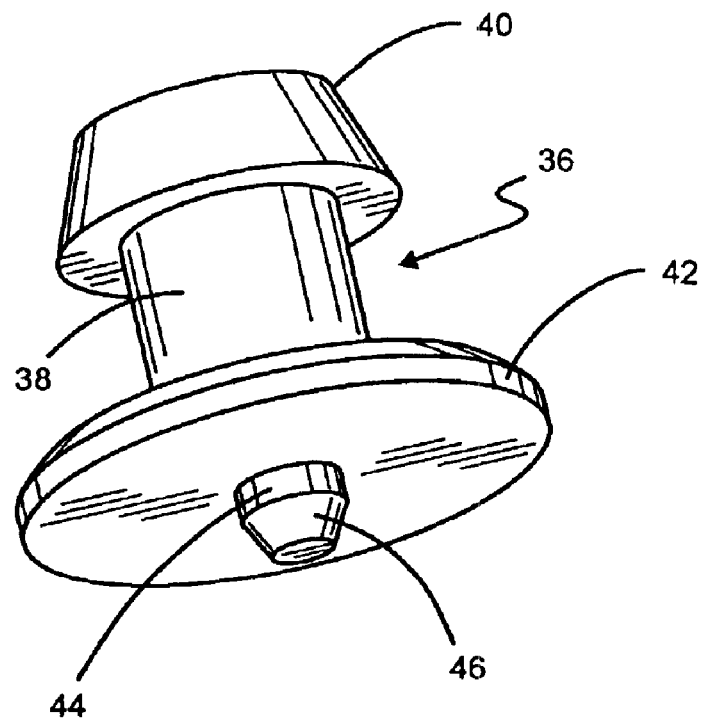
FIG. 3 is a perspective view of an anchor post used in carrying out the method of the present invention.

FIG. 3 shows a perspective view of the combination backfill plug and anchor. It is indicated generally by numeral 36 and comprises a cylindrical midsection 38 with an enlarged, frusto-conical head portion 40 at an upper end thereof and a disk-like foot portion 42 that is of a predetermined size greater than the size of the opening 34. Projecting downward from the center of the foot portion 42 is a plug portion 44. It has a tapered portion 46 to facilitate its being fitted into the opening 34 when it is desired to seal the opening. The maximum diameter of the plug portion 44 is designed to create a friction-fit within the precisely located opening 34. Once the plug portion 44 is inserted through the opening 34 in the header and the foot portion 42 is in abutting relation to the header 20', a laser weld may be made between the header and the perimeter of the foot portion 42, such that the anchor is accurately located on the device. Because the resulting seam is displaced a predetermined distance radially outward from the opening 34, there is a reduced likelihood that any of the gases resulting from this latter welding operation will find their way through the now-plugged opening 34 into the interior of the housing.

Figure 4:
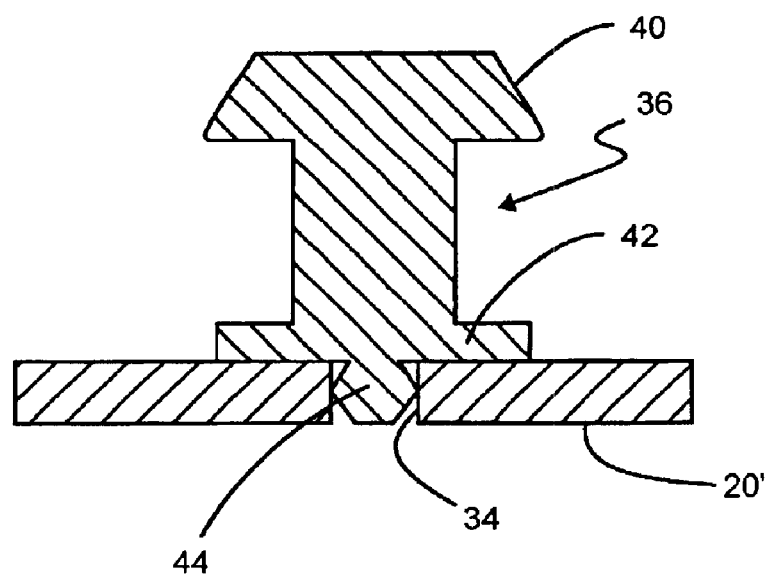
FIG. 4 is an enlarged cross-sectional view of the anchor plug installed on the header of the implantable medical device.

FIG. 4 is a greatly enlarged view of the combination plug and connector block anchor welded in place on the header 20' of the device. The opening 34 contains the plug portion 44 of the device 36 and the foot portion 42 rests atop the header 20' with the anchor head 40 projecting upward. It can be seen from FIG. 4 that the plug portion 44 is designed so as not to intrude into the volume or space within the housing and, thus, does not detract from the volume enclosed by the housing 12' that might otherwise be used for mechanical or electrical components. Furthermore, the backfill opening and anchor/plug can be located in a way that avoids arcing between feed-through wires and/or other circuit components.

Figure 5:
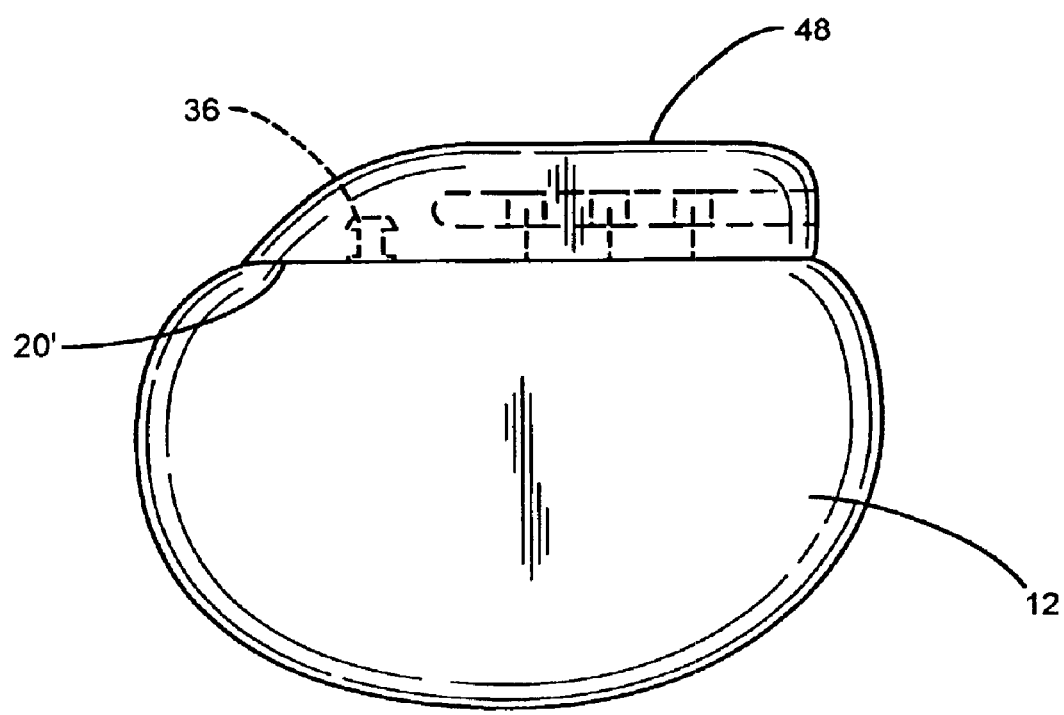
FIG. 5 is a side elevation view of a finished implantable stimulator device.

The partial side view of FIG. 5 shows how the anchor 36 is used to secure the lead connector block to the implantable medical device header. The lead connector block is identified by numeral 48 and is affixed with a known bonding agent to the header 20' of the device 12. The anchor 36 fits into a recess formed in the undersurface of the lead connector block 48 and serves to mechanically secure the lead connector block to the header 20' as the bonding agent cures. The lead connector block 48 is formed from a suitable medical grade plastic. The can or housing 12 may be titanium or stainless steel and, depending on which, the combination plug and lead connector block anchor will be of the same material as the can to facilitate the welding operations.

In that the prior art backfill tube design imposes both a size penalty and a cost penalty, by eliminating it, as in the design of the present invention, additional space becomes available for an increased number of feed-throughs. Moreover, because the plug portion of the device 36 when inserted into the opening 34 holds the device 36 in place so that no additional fixturing is needed during the welding operation. As mentioned, the flange of the foot portion 42 puts the welding instrument well away from the opening 34 helping to preclude unwanted gases from finding their way back into the enclosure.

Furthermore, the method of the present invention better lends itself to batch processing in that a plurality of implantable medical devices can be placed in an evacuable chamber to extract the helium and argon gases from all of them at one time. Likewise, the desired inert gas (nitrogen) can be made to fill the chamber so that all of the devices are backfilled simultaneously. Whereas, the use of a backfill tube requires a further welding step to seal the tube following the backfill step that can result in the reintroduction of contaminants, the plug of the present precludes this from happening.

The placement of the anchor bracket portion of the backfill opening plug is more accurate because such placement is based on the tooling consistency of the opening formed through the can header and does not involve any spot welding tolerances. The lead connector block attachment operation can thus be more precisely predicted, given the fact that the anchor/plug is more accurately placed.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself

What is claimed is:

1. A method of manufacturing an implantable medical device having an electronic circuit and a battery power supply hermetically sealed within a metal housing, the housing having first and second halves and incorporating a feed-through assembly for connecting the electronic circuit to electrical contacts within a lead connector block, the lead connector block being attached to a housing header by anchor posts, comprising the steps of:

(a) welding the first and second halves of the housing together so that the electronic circuit and battery power supply are contained within the housing;

(b) welding the feed-through assembly to the housing header, leaving an opening in the header leading to an interior of the housing;

(c) aspirating the interior of the housing to exhaust gases arising from the welding steps through said opening;

(d) injecting an inert, non-conductive gas through the opening into the interior of the housing;

(e) plugging the opening with an anchor post; and (f) anchoring the lead connector block to the header using the anchor post.

2. The method of claim 1 wherein the plugging step includes:

(a) providing an anchor posts having a cylindrical midsection, an enlarged frusto-conical head portion, a foot portion of a diameter that is of a predetermined size greater than the size of the opening and a plug portion projecting from the foot portion, the plug portion of a size creating a friction fit with the opening;

(b) inserting the plug portion into the opening; and (c) welding the foot portion to the header.

3. An implantable medical device comprising:

(a) a battery powered pulse generator contained within a sealed metal enclosure, said enclosure including a header for supporting a lead connector block thereon;

(b) a gas evacuation and filling port formed through the header to an interior of the enclosure;

(c) a lead connector block anchor disposed in the gas evacuation and filling port for sealing the gas evacuation and filling port; and (d) a lead connector block secured to the header by the lead connector block anchor.

4. The implantable medical device as in claim 3 wherein the lead connector block anchor comprises:

(a) a generally cylindrical mid portion having an enlarged, frusto-conical head at one end of the mid portion and a radially extending circular flange at an opposite end of the mid portion; and (b) an integrally formed plug portion projecting from the circular flange in a direction opposite that of the mid portion, the plug portion being sized to fit into the gas evacuation and filling port with a predetermined friction fit.

5. The implantable medical device as in claim 4 wherein the length of the plug portion is about equal to a thickness dimension of the metal comprising the enclosure so that when inserted into the gas evacuating and filling port, it does not project into an interior space defined by the enclosure.

6. The implantable medical device as in any one of claims 3–5 wherein the metal enclosure and the lead connector block anchor are both titanium.

7. The implantable medical device as in any one of claims 3–5 wherein the metal enclosure and the lead connector block anchor are both stainless steel.

* * * * *